United States Patent [19]
Sahbari et al.

[11] Patent Number: 6,166,254
[45] Date of Patent: Dec. 26, 2000

[54] METHOD OF MANUFACTURING HIGH PURITY AMIDOXIMES FROM HYDROXYLAMINE AND NITRILES

[75] Inventors: Javad J. Sahbari; Jin Wang Russell, both of Sunnyvale, Calif.

[73] Assignee: Silicon Valley Chemlabs, Inc., Sunnyvale, Calif.

[21] Appl. No.: 09/199,400

[22] Filed: Nov. 24, 1998

[51] Int. Cl.[7] .................................................. C07C 249/00
[52] U.S. Cl. .............................................................. 564/253
[58] Field of Search ............................................... 564/253

[56] References Cited

U.S. PATENT DOCUMENTS

| | | |
|---|---|---|
| 3,607,941 | 9/1971 | Bailey . |
| 3,720,714 | 3/1973 | Bailey . |
| 3,897,447 | 7/1975 | Fisher . |
| 3,991,067 | 11/1976 | Gregory et al. . |
| 4,122,257 | 10/1978 | Prossel et al. . |
| 4,142,044 | 2/1979 | Günther et al. . |
| 4,144,391 | 3/1979 | Hatfield . |

*Primary Examiner*—Paul J. Killos
*Attorney, Agent, or Firm*—Pillsbury Madison & Sutro; David H. Jaffer

[57] ABSTRACT

Amidoximes are prepared from aqueous hydroxylamine and nitriles to yield amidoximes. Reaction of acetonitrile with aqueous hydroxylamine at ambient temperature yields acetamidoxime crystals.

10 Claims, No Drawings

METHOD OF MANUFACTURING HIGH PURITY AMIDOXIMES FROM HYDROXYLAMINE AND NITRILES

BACKGROUND OF THE INVENTION

1. Field of the Invention

This invention relates to an improved method for making amidoximes. The method uses an aqueous hydroxylamine solution and a nitrile at ambient temperature.

2. Brief Description of the Prior Art

Amidoximes of general formula R—C(NH$_2$)=NOH, where R is an alkyl or an alkoxy group, are used extensively as intermediates in manufacturing of other products. They are used in the pharmaceutical industry for preparation of a variety of different drugs, in optical brightners for textile materials and synthetic polymers, and in antibacterial and antiparasitic materials (see U.S. Pat. Nos. 3,991,067; 4,142,044; 4,122,257; and 4,144,391).

U.S. Pat. No. 3,897,447 discloses the application of amidoximes in synthesis of anthelmintic agents. The method disclosed for synthesis of acetamidoxime uses hydroxylamine hydrochloride, acetonitrile and potassium carbonate as starting raw materials in a multi-step process. Using raw material of this kind makes the process complicated and difficult. This reaction mixture also requires refluxing the mixture for 16 hours making the reaction process slow, costly and time consuming. In addition, since the starting material contains inorganic anions and cations, the possibility of having ionic contamination is very high, thus making the final product impure. These processes normally give a low production yield due to the multiple steps required. Other amidoximes known in previous art are also prepared using similar methods starting with a corresponding nitrile compound in an alkaline media.

SUMMARY OF THE INVENTION

The present invention is a method that does not require use of an alkaline solution such as potassium hydroxide or potassium carbonate. It does not require a long process time or complicated reaction steps. Instead, the present method uses a simple spontaneous reaction, which increases the product yield.

This method has several advantages over the traditional methods: (a) it is fast and spontaneous therefore giving a high production yield; (b) it does not add any inorganic, organic or ionic impurities during the process; and (c) it does not need a long and difficult process or costly apparatus.

Briefly, in the preferred embodiment, high purity acetamidoxime, CH$_3$—C(NH$_2$)=NOH, can be prepared using free hydroxylamine base and acetonitrile (CH$_3$—CN). A 50% (by weight) aqueous solution of hydroxylamine base is mixed with high purity acetonitrile. The crystalline amidoxime material can be filtered and recrystallized using an inert fluorocarbon solvent for further purification.

DESCRIPTION OF THE PREFERRED EMBODIMENT

The present invention is a method for making high purity amidoximes from an aqueous hydroxylamine solution and nitrites. The example given below uses acetonitrile to yield acetamidoxime. The reaction occurs at ambient temperatures. Those skilled in the art will recognize that analogous nitrites may be used to create other amidoximes.

EXAMPLE 1

45 ml of high purity acetonitrile was added to 90 ml of 50% hydroxylamine/50% water (by weight), and stirred with a magnetic stirrer at 25° C. Crystalline acetamidoxime separated. The mixture was stirred 24 hours at ambient temperature to complete formation of crystals and filtered the next day. The acetamidoxime was purified as follows: The crystals were filtered and then dissolved in a non-polar solvent (perfluorohexane) by heating, and cooled overnight at ambient temperature for recrystallization. The crystalline material was then filtered and washed with perfluorohexane. The melting point was 136° C.–138° C., and the yield approximately 56%. The product was analyzed by FT-IR, GC/MS, NMR, and other methods to confirm the molecular structure. The crystal structure was determined by x-ray methods.

Although the present invention has been described above in terms of a specific embodiment, it is anticipated that alterations and modifications thereof will no doubt become apparent to those skilled in the art. It is therefore intended that the following claims be interpreted as covering all such alterations and modifications as fall within the true spirit and scope of the invention.

What is claimed is:

1. A method for making acetamidoxime comprising the steps of:
   (a) adding acetonitrile to an aqueous hydroxylamine solution having from 30% to 70% by weight hydroxylamine; and
   (b) mixing the acetonitrile and aqueous hydroxylamine solution to cause formation of acetamidoxime, wherein the solution is essentially free of added organic solvents.

2. The method of claim 1, further comprising the step of separating the acetamidoxime.

3. The method of claim 1, wherein the solution is mixed at a temperature of 40° C. or less.

4. The method of claim 1, wherein the hydroxylamine is provided from the aqueous hydroxylamine solution and is not liberated in the solution from ionic precursors, and the solution is essentially free of ionic impurities.

5. A method for making acetamidoxime comprising the steps of:
   (a) adding acetonitrile to an aqueous hydroxylamine solution having from 30% to 70% by weight hydroxylamine; and
   (b) mixing the acetonitrile and aqueous hydroxylamine solution to cause formation of acetamidoxime, wherein the solution is essentially free of added bases.

6. The method of claim 5, wherein the solution is mixed at a temperature of 40° C. or less.

7. The method of claim 5, wherein the hydroxylamine is provided from the aqueous hydroxylamine solution and is not liberated in the solution from ionic precursors, and the solution is essentially free of ionic impurities.

8. A method for making acetamidoxime comprising the steps of:
   (a) adding acetonitrile to an aqueous hydroxylamine solution having from 30% to 70% by weight hydroxylamine; and
   (b) mixing the acetonitrile and aqueous hydroxylamine solution to cause formation of acetamidoxime, wherein the solution is essentially free of added organic solvents and added bases.

9. The method of claim 8, wherein the solution is mixed at a temperature of 40° C. or less.

10. The method of claim 8, wherein the hydroxylamine is provided from the aqueous hydroxylamine solution and is not liberated in the solution from ionic precursors, and the solution is essentially free of ionic impurities.

* * * * *